US006123982A

United States Patent [19]
Fontana

[11] Patent Number: 6,123,982
[45] Date of Patent: Sep. 26, 2000

[54] DENTAL FLOSS

[75] Inventor: Jose Eder Fontana, SaoPaulo, Brazil

[73] Assignee: Colgate-Palmolive Company, New York, N.Y.

[21] Appl. No.: 09/379,190

[22] Filed: Aug. 20, 1999

Related U.S. Application Data

[60] Provisional application No. 60/098,665, Sep. 1, 1998.

[51] Int. Cl.$^7$ .............................. A61C 15/04; B05D 1/38; B05D 1/40; B05D 3/12
[52] U.S. Cl. ..................... 427/2.29; 427/2.31; 427/175; 427/365; 427/381
[58] Field of Search .................. 427/2.29, 2.31, 427/155, 173, 175, 365, 381

[56] References Cited

U.S. PATENT DOCUMENTS

| | | | |
|---|---|---|---|
| 656,479 | 8/1900 | Schellenbach . | |
| 3,277,009 | 10/1966 | Freifeld et al. | 427/155 |
| 3,455,771 | 7/1969 | Ichimi et al. | 427/175 |
| 3,899,614 | 8/1975 | Okamoto et al. | 427/175 |
| 3,930,059 | 12/1975 | Wells | 427/2.29 |
| 4,406,881 | 9/1983 | Ladanyi . | |
| 4,627,975 | 12/1986 | Lynch . | |
| 4,853,213 | 8/1989 | Thame . | |
| 4,911,927 | 3/1990 | Hill et al. | 427/2.29 |
| 4,922,936 | 5/1990 | Buzzi et al. | 132/321 |
| 5,035,252 | 7/1991 | Mondre . | |
| 5,143,949 | 9/1992 | Grogan et al. | 427/155 |
| 5,165,913 | 11/1992 | Hill . | |
| 5,277,928 | 1/1994 | Strandberg | 427/175 |
| 5,294,434 | 3/1994 | King . | |
| 5,300,290 | 4/1994 | Spencer . | |
| 5,312,642 | 5/1994 | Chesterfield et al. | 427/2.31 |
| 5,329,881 | 7/1994 | O'Rourke | 427/2.29 |
| 5,362,515 | 11/1994 | Hayes et al. | 427/155 |
| 5,558,901 | 9/1996 | Gilligan et al. | 427/2.29 |

FOREIGN PATENT DOCUMENTS

| | | |
|---|---|---|
| 2027360 | 4/1992 | Canada . |
| 3049-746 | 7/1989 | Japan . |
| 3228-758 | 2/1990 | Japan . |
| 91/14412 | 10/1991 | WIPO . |
| 97/42907 | 11/1997 | WIPO . |
| 98/00073 | 1/1998 | WIPO . |

*Primary Examiner*—Diana Dudash
*Attorney, Agent, or Firm*—Michael J. McGreal

[57] ABSTRACT

The floss is comprised of a texturized yarn that has been coated and impregnated with a water-soluble polymer and the water-soluble polymer coating cured and set while the yarn is stretched and is under tension. The yarn while stretched and tensioned is at a reduced width, which allows for easier insertion of the yarn floss between teeth. The yarn floss is wound onto a spool in the decreased width condition. For use, a length of floss is removed from the spool and placed between teeth. The saliva in the mouth dissolves the cured and set water-soluble polymer with the floss expanding to fill the space between the teeth. The floss is optionally coated with flavors, medicants and other substances. These can be synthetic or naturally occurring substances such as herbal substances.

19 Claims, No Drawings

DENTAL FLOSS

This application is a provisional of 60/098,665, filed Sep. 1, 1998, still pending.

FIELD OF THE INVENTION

This invention relates to a texturized dental floss that has a relatively narrow initial cross-section. More particularly this invention relates to a texturized dental floss that is maintained in an unexpanded and relatively narrow cross-section until use, and, which during use, expands to an expanded and relatively thick cross-section.

BACKGROUND OF THE INVENTION

Texturized dental flosses are used by persons who have large inter dental spaces and who have bridges and various dental prosthesis. The texturized flosses have a greater diameter and are more effective in removing food debris and other material from large inter dental spaces, from under bridges and from around various dental prosthesis. The larger diameter and the fibrous nature of the flosses provide a good cleaning action. These texturized flosses are used in many instances in conjunction with a conventional multifilament floss or a tape floss. The filament floss or tape floss is used to remove food debris and other material from between the tighter inter dental spaces. The use of both flosses provides for a good cleaning of all inter dental spaces, bridgework and other prosthesis prior to tooth brushing. A tooth brushing with an antiplaque, antitartar, antibacterial or other dentifrice completes an effective regimen of oral care.

The state-of-the-art of texturized flosses is exemplified by the texturized flosses and the methods of making these flosses as described in U.S. Pat. No. 4,008,727, U.S. Pat. No. 4,277,297 and U.S. Pat. No. 3,896,824. In U.S. Pat. No. 4,008,727 there is disclosed a texturized floss that has intermittent texturized portions and string portions. A similar texturized floss is described in U.S. Pat. No. 3,896,827. This texturized floss likewise has texturized portions and string portions. Each of these patents discloses a coating process where by the selective use of tension texturized and non-texturized portions are formed. This method for making texturized flosses with texturized portions and non-texturized portions is further described in U.S. Pat. No. 4,277,297.

These prior art texturized flosses are available in various set thicknesses. However, due to the coatings on the texturized material, and the intermittent threader and texturized portions, the flosses overall are quite rigid. These texturized flosses can be in a continuous strand or in separate lengths and usually are in separate lengths. The threader portion is a stiff narrow diameter portion. The texturized floss portion will have a larger diameter portion which is a brushing portion. The thickness of the texturized portion is set in a narrow range for each floss size. However, it is desired to have a texturized floss where there the thickness changes during use and with tension. The floss then can be used for a wide range of interdental spaces.

This new floss in the initial relatively narrow cross-section can be fitted into narrow interdental spaces. As a water-soluble coating on the floss dissolves, the floss strand will decrease in length to a more relaxed state and increase in the cross-sectional dimension. This aids in the flossing since there will be a greater contact with the teeth surfaces in the interdental spaces. There is provided a texturized floss that is easy to insert into tight interdental spaces, and which during the flossing operation expands to fill the interdental space for enhanced flossing.

BRIEF SUMMARY OF THE INVENTION

The texturized dental floss of this invention is a texturized floss that has a reduced diameter, but during flossing, expands in diameter to better fill and clean the larger interdental spaces. The dental floss has a water-soluble coating which upon contact with saliva dissolves and allows the texturized floss to expand to approximately the diameter prior to stretching and coating.

The texturized floss is made from a yarn that is comprised of a plurality of bundles of filaments. These are sometimes referred to as bundles. In each filament handle there can be 20 or more filaments. The filaments have been texturized by forced air, mechanical or heat treatments to form coils, curves, twists, crimps and/or loops. These yarns have the property of being stretchable whereby the cross-section is reduced under tension. These yarns can solely be coated with a water-soluble polymer or first can be coated with a non-water-soluble polymer to bond the fibers in place so as to prevent shredding during use as a floss and then coated with the water-soluble polymer. When solely coated with a water-soluble polymer, the coating will serve to sufficiently bind the fibers to prevent fraying and will maintain the yarn in the stretched condition in which there were coated and cured. The coating can be conducted while the yarn is in a tensioned, stretched condition or in a non-tensioned, non-stretched condition. The curing is conducted while the yarn is in a tensioned stretched condition. The coated yarn preferably is calandered such as by passing through nip rolls to flow the polymer into the yarn fibers prior to curing. When first coated with a non-water-soluble polymer, this coating preferably is applied and cured while the yarn is under a minimal tension. This preserves the stretch characteristics of the yarn. After curing, the floss is coated with a water-soluble coating, this coated yarn preferably calandered to flow the polymer into the fibers, and cured while the floss is in a stretched condition.

The result in either case is a texturized floss that has a reduced diameter. This reduced diameter floss can readily be inserted into tight interdental spaces. During use the water-soluble coating dissolves with the diameter of the floss increasing as the tension on the floss is reduced. The relaxed floss form then fills the space and better removes plaque and food from between teeth.

Prior to, or during the coating of the floss with the water-soluble polymer, an additive such as a flavorant, colorant and/or medicant can be added. The result is the texturized floss after the final curing containing such a flavorant, colorant or medicant. The flavorants include peppermint, spearmint, cinnamon, fruit and herbal flavors. The medicants include fluoride, densitizing agents, antiplaque agents, antitartar agents, antibacterials, antiseptics, coagulants and other medicants. Preferably the floss will contain a flavorant and medicant.

DETAILED DESCRIPTION OF THE INVENTION

The yarn that is to be used as the floss is a particular yarn. It consists of a plurality of bundles of filaments. These are sometimes referred to as cables. In each filament bundle there can be perhaps 20 or more filaments. The filaments have been texturized by forced air, mechanical and/or heat treatments to form coils, curves, twists, crimps and/or loops. These yarns have the property of being stretchable so that the cross-sectional diameter of the yarn will be reduced when the yarn is under tension. When not under tension the yarn will regain substantially its original length and cross-sectional diameter. This in combination with an irregular honeycomb surface on the yarn results in the yarn being an effective dental floss. The yarn can be tensioned to reduce its diameter to facilitate placing the yarn between a persons teeth, and then relaxed to increase the diameter for use as a floss. This cleans food debris and other materials from between close interstitial spaces.

The yarn will be comprised of about 4 to 10 filament bundles, and preferably about 6. The yarn at rest will have a cross-sectional diameter of about 10 mm to 40 mm, and preferably about 15 mm to 30 mm. In general, the yarn will approximate a circular cross-section. Upon stretching, the cross-sectional diameter of the yarn can be reduced to about as low as 10 percent of its non-tensioned diameter. In length it can be increased up to about 150 percent of its original non-tensioned length when put under tension. These are useful properties for the yarns when used as a dental floss. The floss can be inserted into inter dental spaces when tensioned and used to remove food debris when in a relaxed, increased cross-sectional diameter form.

The yarns cannot be used directly as a floss. There is a tendency for the yarns to shed parts of filaments. If used directly as a floss filament, parts of the yarn can be left between teeth. This is annoying and is not considered to be acceptable to a person who is flossing. Consequently, the yarn is coated with a coating to lock/bond/network the filaments into a yarn. The coating preferably is a substantially water soluble polymer that will wet the filaments of the yarn and which can be set by solvent evaporation or other polymerization. In the alternative, non-water soluble polymers also can be used as a first coating followed by a coating with a water-soluble polymer. When first coated with a non-water-soluble polymer, this coating, and the subsequent curing, are conducted with the yarn under minimal to no tension as described in U.S. application Ser. No. 08/648,332 filed May 15, 1996. Only enough tension is used to move the yarn through the coating process. Polymers set by solvent evaporation are set by the evaporation of the solvent through heating. The solvent can be water or an organic. In any regards, the end result is a dental floss with the filaments locked into the yarn structure. However, the yarn retains its original characteristics as set out above. It is stretchable. The coated yarn under tension can acquire about as low as 10 percent of the cross-sectional diameter of the yarn at rest. And the coated yarn can stretch to more than 150 percent of its length as compared to the yarn under no tension.

As discussed, the yarn can be pretreated with a polymer to lock/bond/network the filaments of the yarn together. In such an instance the pretreatment can be with a range of polymers. These can be water-soluble or water-insoluble polymers. When the yarn is so pretreated, the objective is to maintain, as much as possible, the original cross-section of the yarn. Consequently, the yarn is coated with the polymer and the polymer cured on the yarn while the yarn is under minimal to no tension. The only tension on the yarn is that needed to pull the yarn through the polymer coating bath. The curing preferably is conducted while the yarn is moving downward solely under its own weight. That is, the only tensioning force is a gravitational force. This pretreatment prevents the yarn from fraying when used as a floss.

In the main treating step, the yarn, virgin or pretreated, is coated with a water-soluble polymer. The yarn then passes through nip rolls to remove excess polymer and to further impregnate the polymer into the yarn. The yarn then is maintained under a tension during curing of the water-soluble polymer so as to substantially decrease the cross-sectional dimension of the yarn. The tension is such that the cross-section dimension is decreased up to 90%, with the yarn being elongated to more than 150% of its original length. The yarn is cured while in this tensioned form. The coating can be by immersion by passing the yarn through a polymer bath, roller coating or spray coating. A preferred technique is by immersing the tensioned yarn in a polymer bath. In addition the coating can be applied in one or more stages. A two-stage coating process is preferred with the yarn under tension in each stage. This preferred process is comprised of a first polymeric solution coating followed by a second coating with a flavor and/or medicant solution. However the first polymeric solution can contain flavorants and/or medicants.

After coating any excess polymer can be removed by passing between nip rolls and optionally through a calandering system to impregnate the polymer into the tensioned yarn. Preferably there is a single calandering after the second stage coating. However there can be a calandering after each stage of coating. The coated and calandered yarn thereafter passes to a curing station, which usually is a solvent removal station. The solvent usually is water but can be an organic or a water/organic mixture. After the coating has been set by solvent removal or other polymerization technique, the coated yarn, which now is the floss, is wound onto a spool. These can be larger spools for professional use or smaller spools for personal use.

As noted, in the first stage or second stage coating solutions there can be flavorants and various medicants, alone and in various combinations. The flavorants include eucalyptus, peppermint, wintergreen, spearmint, tee tree oil, sage oil, licorice, cinnamon and fruit flavors such as orange and lemon, and herbal flavors. The medicants include fluoride, densitizing agents, antitartar agents, antiplaque agents, antibacterials, herbs, antifungal agents, antiprotozoan agents, antiseptics and coagulants. The various medicants can be synthetic or naturally occurring. There are many naturally occurring agents that have medicant properties. These naturally occurring agents include chamomile tincture, myrrh tincture, aloe vera, nicotine, sanguinaria, chelerythine and benzophenanthridine alkaloids.

The flavorant and/or medicant is solubilized or emulsified in the water-soluble polymer solution, which usually is an aqueous solution. It preferably is applied to the yarn by immersion of the yarn in the solution, calandering to impregnate the polymer and the other coating components into the yarn, and curing the yarn by removing the water or water/organic solvent. The coating will be applied in one or more stages. Preferably it will be conducted in two stages. The yarn will contain about 20% to about 60% by weight of cured polymer solution plus flavorants and/or medicants, and preferably about 30% to about 50% by weight of cured polymer plus flavorant and/or medicant. The cured water-soluble polymer will be on the yarn in a content of about 5% to about 12% by weight. If there is a pretreatment polymer content this will be in addition to the content of the cured water-soluble polymer content.

The useful pretreatment polymers include polyurethanes, polyesters, polyamides such as nylons, vinyl alcohol homopolymers and copolymers, vinyl acetate homopolymers and copolymers. Various polyurethanes can be ultraviolet cured. Useful solvent based polymers include vinyl acetate copolymers, vinyl alcohol copolymers and nylon dissolved in a water, ethanol, or ethanol/water mixture. When the solvent is evaporated the polymer sets to keep the filaments locked to the yarn and the yarn in the cross-sectioned structure in which the polymer has been set.

Suitable water soluble polymers include vinyl alcohol polymers and copolymers, vinyl acetate polymers and copolymers and copolymers of vinyl acetate/ethylene copolymer. The water-soluble polymer will be applied to the yarn so as to comprise about 3% to about 15% of the yarn. As noted, the coating can be applied by immersion in a bath, by being passed over a coating roller, by being passed through two coating rollers and by being sprayed with the water-soluble polymer.

In use a section of the floss is cut from the remainder of the spool and used as a floss. During use the floss will increase in diameter about 3 to 10 times as the water-soluble polymer is dissolved. This floss is easy to thread into tight interdental spaces, and during use increases in diameter to fill the interdental space. This provides for better removal of food and other debris.

The present invention will be disclosed in more detail with reference to the following example.

EXAMPLE 1

A nylon 66 polyamide texturized yarn having a denier of 948, 34 filaments and two-ply (DuPont Merge 697) is coated with a coating formulation having the following concentration of components:

| Ingredients | % by Weight |
| --- | --- |
| Polyvinyl acetate/ethylene copolymer(Airflex 400) | 20.5 |
| Cremephor RH 40 (castor oil hydrogenated) | 4.0 |
| Xylitol | 2.0 |
| Sodium saccharin | 0.15 |
| Chamomile tincture | 0.475 |
| Myrrh tincture | 0.95 |
| Polyethylene glycol 6000 | 23.025 |
| Polyethylene glycol 400 | 6.0 |
| Sage oil | 0.19 |
| Tea tree oil | 0.285 |
| Flavor Sorriso Herbal KB-8112-1-11 | 19.0 |
| Glyceryl triacetate (triacetin) | 1.5 |
| Water | to 100% |

The yarn which has a large cross-section diameter is tensioned to a decreased diameter and pulled through a two stage coating bath. The first bath contains the polymer, (PVA/E copolymer as a 55% emulsion), cremophor, xylitol, sodium saccharin, chamomile tincture and myrrh tincture along with about an equivalent weight of water. The second stage will contain the PEG 6000, PEG 400, herbal flavor, sage oil, tea tree oil and glyceryl triacetate. This second stage coating does not contain any water. The yarn after coating is passed through a curing oven to remove the solvent which primarily is water. The curing oven is maintained at a temperature to remove the water solvent. The residence time of the coated yarn in the curing process over is about 4 to 60 seconds depending on the temperature of the curing oven.

The end product texturized yarn floss has the following concentration of components:

| Ingredients | % by Meter of Finished Product |
| --- | --- |
| Nylon semitexturized raw yarn | 61.728 |
| Polyvinyl acetate/ethylene copolymer | 7.385 |
| Cremephor RH 40 (castor oil hydrogenated) | 2.620 |
| Xylitol | 1.310 |
| Sodium saccharin | 0.098 |

-continued

| Ingredients | % by Meter of Finished Product |
| --- | --- |
| Chamomile tincture | 0.311 |
| Myrrh tincture | 0.622 |
| Polyethylene glycol 6000 | 11.939 |
| Polyethylene glycol 400 | 3.111 |
| Sage oil | 0.099 |
| Tea tree oil | 0.148 |
| Flavor Sorriso Herbal KB-8112-1-11 | 9.851 |
| Glyceryl triacetate (triacetin) | 0.778 |
| TOTAL | 100.0 |

The floss is easy to thread into and through various sized interdental spaces. During flossing the moisture in the mouth partially dissolves the water soluble polymer and the floss expands to fill the interdental space being flossed.

What is claimed is:

1. A method for making a texturized dental floss comprising:
   (a) coating a texturized yarn in at least a first coating stage with a water-soluble polymer;
   (b) passing said coated yarn through a unit to remove excess water-soluble polymer coating and to flow the water-soluble polymer into said coated yarn;
   (c) stretching said coated yarn to reduce the cross-sectional diameter thereof and curing said water-soluble polymer while said coated yarn is under a tension of at least 125% of its relaxed state by the removal of water, the curing of the water-soluble polymer producing a cured texturized yarn having a reduced cross-sectional diameter; and
   (d) coating said cured texturized yarn in a coating stage after curing the water-soluble polymer with an additional substance to enhance the use of the cured texturized yarn as a floss.

2. A method as in claim 1 wherein said texturized yarn has a thickness of about 10 mm to about 40 mm at relaxation and a thickness of about 1 mm to about 4 mm at a tension of more than about 10 grams.

3. A method as in claim 1 wherein said water-soluble polymer is selected from the group consisting of homopolymers and copolymers of vinyl acetate and vinyl alcohol.

4. A method as in claim 1 wherein a composition containing said water-soluble polymer further contains at least one of a flavorant and a medicant.

5. A method as in claim 1 wherein said texturized dental floss has a coating content of about 20% to about 60% by weight of the total weight of said texturized dental floss.

6. A method as in claim 5 wherein said coating content of said texturized dental floss is about 30% to about 50% by weight.

7. A method as in claim 4 wherein said medicant is a naturally occurring medicant.

8. A method as in claim 1 wherein in step (d), a wax coating is applied to said texturized yarn.

9. A method as in claim 1 wherein said coating of said yarn is applied while said yarn is in a tensioned condition.

10. A method as in claim 1 wherein in step (b) said coated yarn is passed through rollers to remove excess polymer and to flow said polymer into said yarn.

11. A method for making a texturized dental floss comprising:
   (a) coating a texturized yarn with an agent to stabilize said yarn from shredding and fraying, said coating being applied to said yarn and cured thereon while said yarn over its full length is in an essentially relaxed condition;

(b) coating the coated texturized yarn with a water-soluble polymer composition to produce a further coated texturized yarn;

(c) stretching the further coated texturized yarn to an elongated condition; and (d) curing the coating on the stretched texturized yarn to thereby maintain the stretched texturized yarn in an elongated condition.

12. A method as in claim 11 wherein said texturized yarn has a thickness of about 10 mm to about 40 mm at relaxation and a thickness of about 0.1 mm to about 4 mm at a tension of more than about 10 grams.

13. A method as in claim 11 wherein said agent to stabilize the texturized yarn is a polymer dissolved in a solvent.

14. A method as in claim 11 wherein said water-soluble polymer coating is selected from the group consisting of homopolymers and copolymers of vinyl acetate and vinyl alcohol.

15. A method as in claim 11 wherein prior to step (c), coating the texturized yarn with a substance selected from the group consisting of medicants, colorants and flavorants.

16. A method as in claim 15 wherein said medicant is selected from the group consisting of fluoride, desensitizing agents, antiplaque agents, antitartar agents, antibacterials, antiseptics and coagulants.

17. A method as in claim 11 wherein subsequent to step (d), said texturized yarn is coated with a wax.

18. A method as in claim 11 wherein said coating of said yarn with a water-soluble polymer is conducted while said yarn is in a tensioned condition.

19. A method as in claim 11 wherein said coated yarn is passed through rollers to remove excess polymer and to impregnate said polymer into said yarn.

* * * * *